(12) United States Patent
Maeda et al.

(10) Patent No.: US 8,382,979 B2
(45) Date of Patent: Feb. 26, 2013

(54) LIQUID CHROMATOGRAPH SYSTEM

(75) Inventors: Yoshiki Maeda, Kyoto (JP); Kenichi Yasunaga, Uji (JP); Shinji Tanaka, Osaka (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/541,193

(22) Filed: Jul. 3, 2012

(65) Prior Publication Data

US 2013/0000390 A1    Jan. 3, 2013

Related U.S. Application Data

(62) Division of application No. 13/379,603, filed as application No. PCT/JP2010/060986 on Jun. 28, 2010, now Pat. No. 8,236,175.

(30) Foreign Application Priority Data

Jun. 29, 2009    (WO) .................. PCT/JP2009/002990

(51) Int. Cl.
   *B01D 15/08*    (2006.01)
(52) U.S. Cl. ..................................... 210/198.2; 210/656
(58) Field of Classification Search .................. 210/635, 210/656, 659, 101, 143, 198.2; 73/61.55, 73/61.56; 137/625.11, 625.46
   See application file for complete search history.

(56) References Cited

U.S. PATENT DOCUMENTS

| | | | |
|---|---|---|---|
| 4,625,569 A | 12/1986 | Toei et al. | |
| 6,129,840 A | 10/2000 | Kitaoka | 210/198.2 |
| 6,537,451 B1 | 3/2003 | Hotier | 210/198.2 |
| 7,566,396 B2 | 7/2009 | Iwata | 210/198.2 |
| 7,699,990 B2 | 4/2010 | Deguchi et al. | 210/656 |
| 8,048,312 B2 | 11/2011 | Deguchi et al. | 210/656 |
| 2006/0042686 A1 | 3/2006 | Gamache et al. | 137/51 |
| 2009/0145205 A1 | 6/2009 | Hochgraeber et al. | 73/61.55 |
| 2010/0058841 A1 | 3/2010 | Wilen | 73/61.56 |
| 2010/0101989 A1 | 4/2010 | Berndt | 210/188 |
| 2010/0206411 A1 | 8/2010 | Maeda et al. | |
| 2011/0315633 A1 | 12/2011 | Cormier et al. | 210/656 |

FOREIGN PATENT DOCUMENTS

| | | |
|---|---|---|
| JP | 49-039833 | 4/1974 |
| JP | 60-149973 | 8/1985 |
| JP | 61-23363 | 10/1986 |
| JP | 04-204156 | 7/1992 |
| JP | 2008-215494 | 9/2008 |
| WO | 2009-041442 | 4/2009 |

OTHER PUBLICATIONS

International preliminary report on patentability dated Jan. 4, 2012 and its English language translation issued in corresponding PCT/JP2010/060986 cites the foreign patent documents above.

*Primary Examiner* — Ernest G Therkorn
(74) *Attorney, Agent, or Firm* — DLA Piper LLP (US)

(57) ABSTRACT

A channel-switching valve into which a high-pressure liquid and a low-pressure liquid flow is provided. The channel-switching valve includes a stator and a rotor which has a surface in contact with one surface of the stator and rotates while sliding on the contact surface. The stator has a plurality of liquid flow ports open to the contact surface, and the rotor has a plurality of channel grooves for connecting the liquid flow ports. One of the channel grooves is a straight groove passing through the rotational center of the rotor, and the other channel grooves are line-symmetrically arranged with respect to the straight channel groove. Alternatively, among the channel grooves, the channel grooves into which the high-pressure liquid flows are configured to be located on both sides of the rotational center of the rotor. Thus, a local load acting on the rotor during a high-pressure liquid-feeding process is reduced.

2 Claims, 9 Drawing Sheets

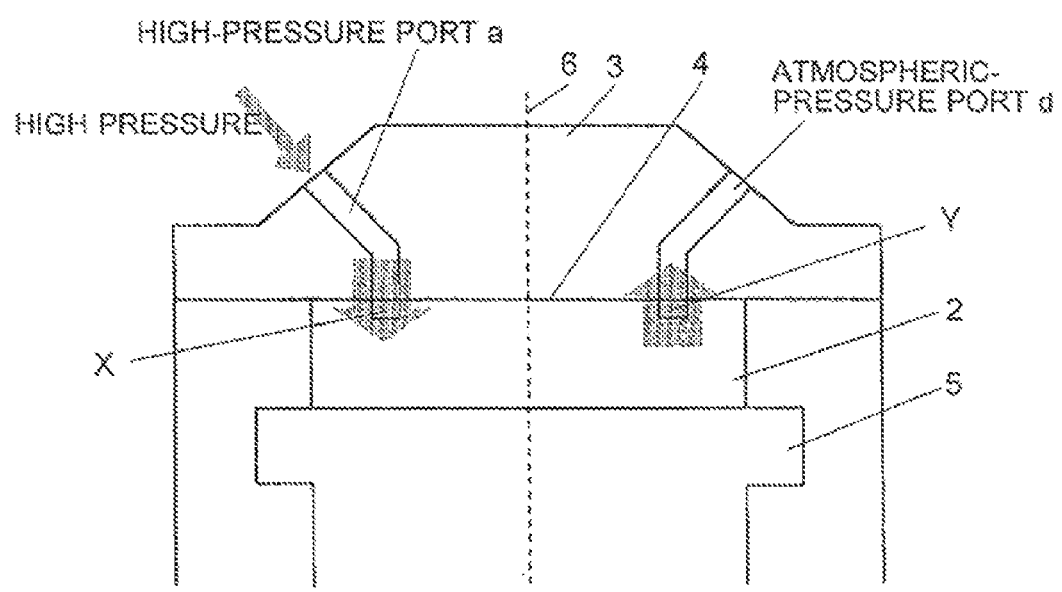

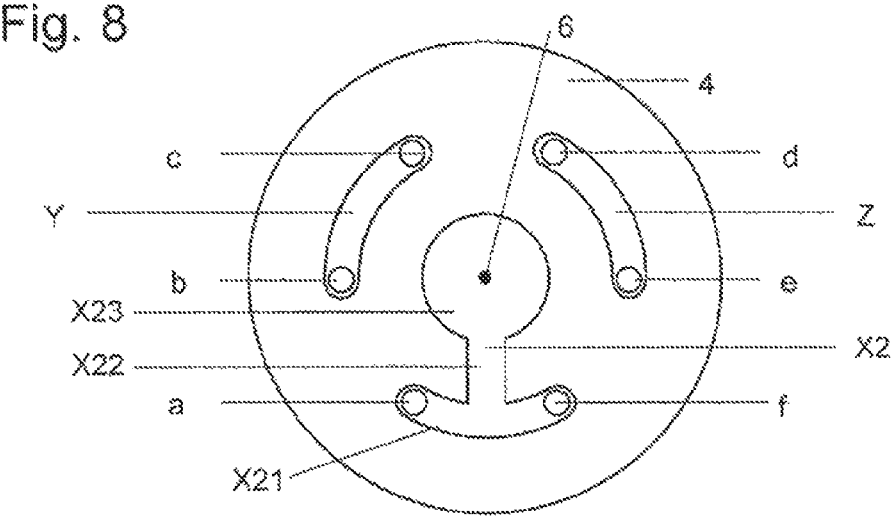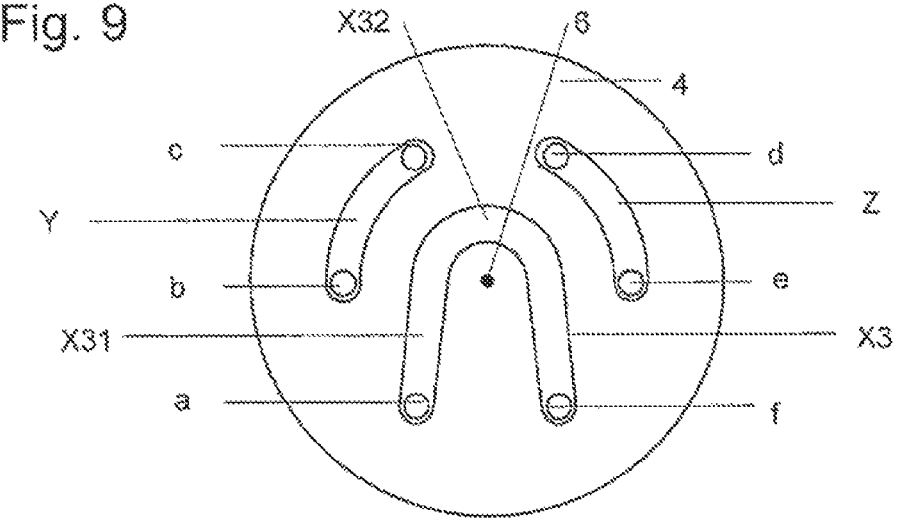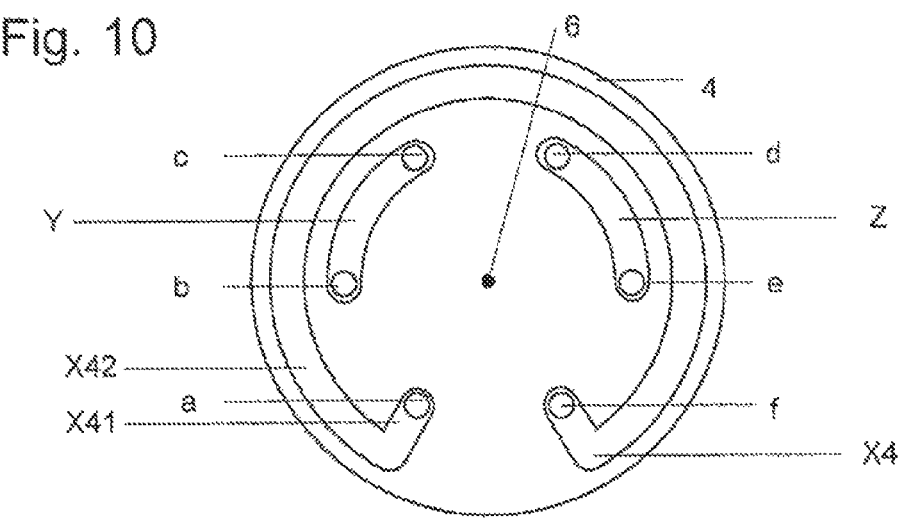

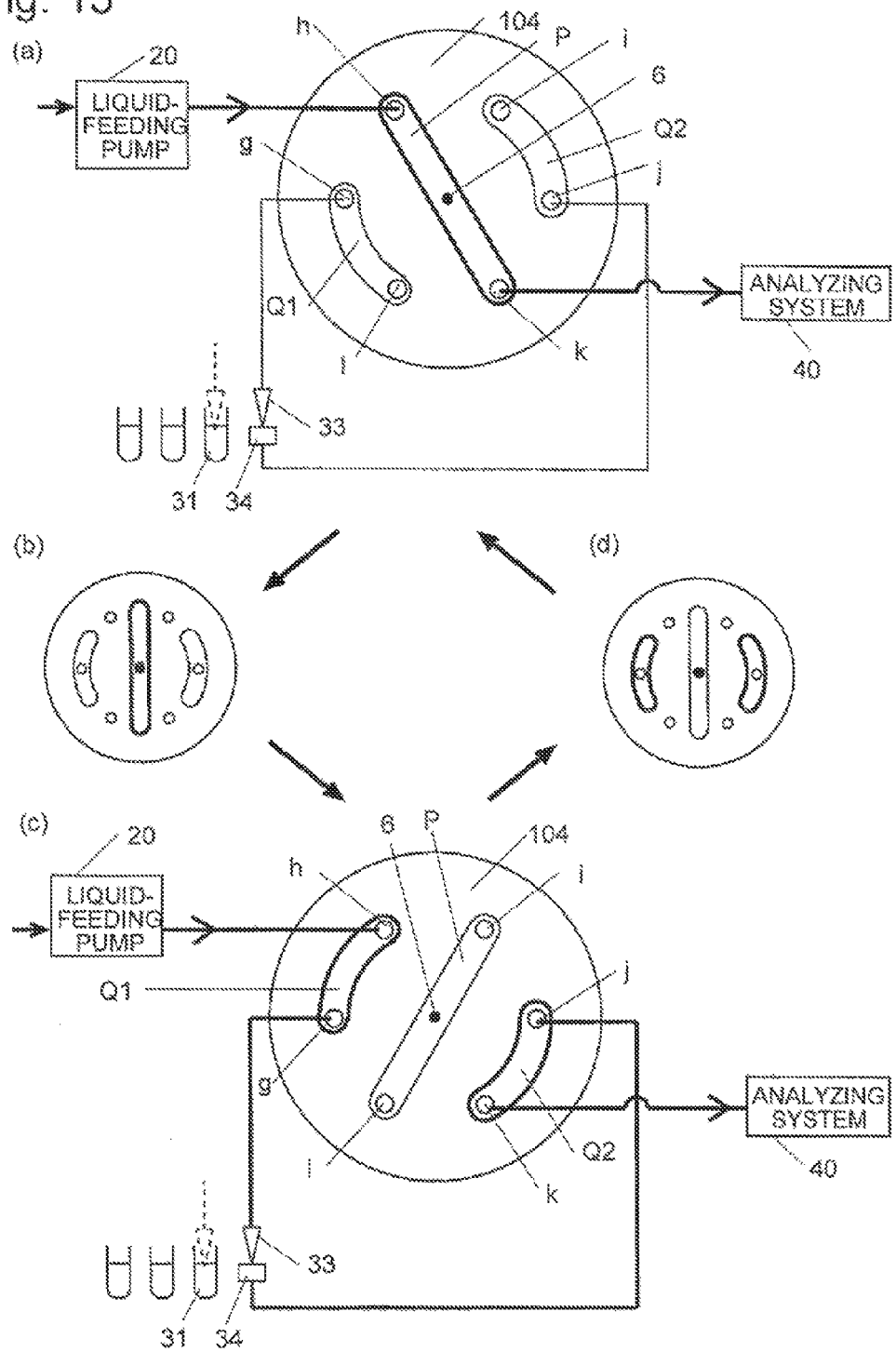

LIQUID CHROMATOGRAPH SYSTEM

This is a divisional application of application Ser. No. 13/379,603 filed Dec. 20, 2011 now U.S. Pat. No. 8,236,175, which in turn is a national phase application of PCT/JP2010/060986 filed Jun. 28, 2010, which in turn claims the benefit of PCT/2009/002990 filed Jun. 29, 2009. The entire contents of PCT/JP2010/060986 and PCT/2009/002990 are incorporated herein by reference.

TECHNICAL FIELD

The present invention relates to a channel-switching valve used in a sample introducing device for introducing a liquid sample into an analytical instrument, and more specifically to a channel-switching valve for a liquid sample introduced at high pressure.

BACKGROUND ART

To analyze a number of liquid samples in a predetermined order by an analyzing system, it is necessary to change the channel in a "sample introducing device", i.e. a device for introducing samples into the analyzing system. FIG. 1 schematically shows a typical channel system for liquid samples in an analysis of the liquid samples. The sample introducing device 30 includes sample containers 31, each of which holds a liquid sample, a washing liquid container 32 holding a washing liquid, a sampling needle 33, an injection port 34 and other components. The injection port 34 and the liquid contained in the washing liquid container 32 are respectively connected, via a channel-switching valve 1, to a channel extending from a liquid-feeding pump 20. The liquid-feeding pump 20 supplies a mobile phase from a mobile-phase container 10 to the sample introducing device 30. Inside the sample introducing device 30, the channel-switching valve 1 is operated so that a number of liquid samples are sent into the channel and carried to an analyzing system 40 in a predetermined order.

The sample introducing device 30 receives high-pressure liquid from the liquid-feeding pump 20. Taking this into account, a valve as shown in FIGS. 2A and 2B is used as the channel-switching valve 1, in which a disk-shaped rotor 2 provided with channel grooves is mounted on a disk-shaped stator 3 having a plurality of ports and is rotated while sliding on the stator 3. In this channel-switching valve 1, the stator 3 has a plurality of ports a-f (only the ports a and d are shown in FIG. 2A) each of which can be connected to one of the channels, with the slidable rotor 2 being mounted on the stator 3. The rotor 2 is pressed onto the stator 3 by a shaft 5 supported by an elastic member, such as a spring (not shown), so as to maintain the liquid-tightness of the channel. FIG. 2B is a plan view of the contact surface 4 of the rotor 2 in contact with the stator 3. The openings of the ports a-f of the stator 3 are also shown. The contact surface 4 is provided with arc-shaped channel grooves X, Y and Z for connecting the openings of the ports a-f. A channel is formed by connecting the channel groves X, Y and Z to the openings of the ports a-f. The combinations of the ports connected by the channel groves X, Y and Z can be changed by revolving the rotor 2 around the rotational center 6. Thus, the channel can be switched. Typically, the stator 3 is made of a metal or ceramic, while the rotor 2 is made of a resin.

BACKGROUND ART DOCUMENT

Patent Document

Patent Document 1: WO-A1 2009/041442
Patent Document 2: JP-A 2008-215494

DISCLOSURE OF THE INVENTION

Problem to be Solved by the Invention

In some types of analyzing systems used in recent years, such as a high-performance liquid chromatograph, liquids are fed at higher pressures than in the conventional systems. In the case where the liquid-feeding pump supplies a liquid at a high pressure (e.g. at 50 MPa or higher), a high-pressure liquid flows from the port connected to the liquid-feeding pump 20 into a channel groove of the rotor 2.

FIG. 3 shows a cross section of the channel-switching valve 1 passing through the ports a and d in a high-pressure liquid-feeding process. Similar to FIG. 2B, the openings of the ports a and d shown in this figure are respectively connected to the channel grooves X and Y. The channel extending from the high-pressure liquid-feeding pump 20 is connected to the port a, allowing high-pressure liquid to flow into the channel groove X connected to the port a. Meanwhile, the ports which are not connected to the channel groove X are connected to the other channel grooves at approximately atmospheric pressure. Therefore, the pressure at the openings of the ports c-f is approximately as low as atmospheric pressure. The rotor 2, which is pressed onto the stator 3 by the shaft 5 supported by a spring to maintain the liquid-tightness of the channel, will be slightly inclined when high pressure is applied to only a portion of the rotor 2. That is to say, when a high-pressure liquid flows into one port, i.e. port a, a portion of the contact surface 4 opposing to the opening of the high-pressure port a across the rotational center 6, i.e. a portion around the opening of the port d, will be more strongly pressed onto the stator 3 than the other portions. If the rotor 2 is revolved in such an inclined state, the contact surface 4 of the rotor 2, which is made of a softer material than the stator 3, will be damaged or abraded.

The damage and abrasion of the contact surface 4 of the rotor, which occurs in the channel-switching operation, are hereinafter described by means of FIGS. 4A-6D.

FIGS. 4A-4D are plan views of the contact surface of the rotor 2 in contact with the stator 3, illustrating the channel-switching operation from the position where the ports a and b communicate with each other to the position where the ports a and f communicate with each other. In FIG. 4A, which shows the position where the ports a and b communicate with each other, the port d located opposite to the high-pressure port a communicates with the port c through the channel groove Y. In FIG. 4D, which shows the position where the ports a and f communicate with each other, the port d communicates with the port e through the channel groove Z. FIG. 4B shows the state immediately after the beginning of the switching operation from the state shown in FIG. 4A. FIG. 4C shows the position where the rotor 2 has been further revolved from the position of FIG. 4B to a position where the port d is located between the channel grooves Y and Z. FIGS. 5A and 5B show cross sections passing through the ports a and d in the states shown in FIGS. 4A and 4B, respectively. FIGS. 6A-6D show cross sections along the channel grooves in a region near the contact surface 4 between the stator 3 and the rotor 2 in the states as shown in FIGS. 4A-4D, respectively.

As shown in FIGS. 4A-4D, during the switching operation from the position where the ports a and b communicate with each other to the position where the ports a and f communicate with each other, the high-pressure port a is connected to the channel groove X, so that a portion of the rotor 2 near the channel groove X is pressed downward by the high pressure. This pressure makes the rotor 2 slightly inclined (see FIGS. 5A and 5B), causing the contact surface 4 of the rotor 2 to be strongly pressed onto the stator 3 at a section opposite to the channel groove X and overloaded. In the state shown in FIG. 4A, the overloaded section of the contact surface 4 (hereinafter, the "loaded section") is located between the ports d and e (see FIG. 6A). A cross section passing through the ports a and d in this state is shown in FIG. 5A. For convenience of explanation, the inclination of the rotor 2, which is actually very slight, is exaggeratingly shown in FIGS. 5A through 6D.

However, starting from the position shown in FIG. 4A, when the rotor 2 is slightly revolved counterclockwise (FIG. 4B), a portion of the loaded section of the rotor 2 is slid under the port d (FIGS. 5B and 6B). In particular, when the rotor 2 is revolved from the position of FIG. 4A, the loaded section slightly protrudes into port d, and the protruded portion is scraped off by the edge 7 of the opening of the port d.

Therefore, if the rotor 2 is further revolved from the position of FIG. 4B through the position of FIG. 4C to the position of FIG. 4D, the loaded section will be continuously scraped off by the edge 7.

Since the scraping of the loaded section by the edge 7 occurs at every channel-switching operation, the scraping-off and damage on the contact surface 4 of the rotor 2 increase as the channel-switching operation is repeated. This may cause an extension of the channel groove, resulting in a switching of the channel at an unintended timing. In a worst case, the neighboring channel grooves may be connected.

The present invention has been developed in view of such problems and is aimed at preventing the contact surface from being scraped off by the edge of the opening of a port during the rotation of the rotor.

Means for Solving the Problems

The first aspect of the present invention aimed at solving the previously described problems is a channel-switching valve into which a high-pressure liquid and a low-pressure liquid flow, the channel-switching valve including a stator and a rotor which has a surface in contact with one surface of the stator and rotates while sliding on the contact surface, the stator having a plurality of liquid flow ports open to the contact surface, and the rotor having a plurality of channel grooves for connecting the liquid flow ports, wherein, among the channel grooves, a channel groove into which the high-pressure liquid flows is configured to be located on both sides of the rotational center of the rotor.

The second aspect of the present invention aimed at solving the previously described problems provides a channel-switching valve, including a stator and a rotor which has a surface in contact with one surface of the stator and rotates while sliding on the contact surface, the stator having a plurality of liquid flow ports open to the contact surface, and the rotor having a channel groove for connecting the liquid flow ports, wherein the channel groove is configured to be located on both sides of the rotational center of the rotor.

The third aspect of the present invention aimed at solving the previously described problems provides a channel-switching valve including a stator and a rotor which has a surface in contact with one surface of the stator and rotates while sliding on the contact surface, the stator having a plurality of liquid flow ports open to the contact surface, and the rotor having a plurality of channel grooves for connecting the liquid flow ports, wherein:

one of the channel grooves is a straight channel groove passing through the rotational center of the rotor; and the other channel grooves are line-symmetrically arranged with respect to the straight channel groove.

Effect of the Invention

In the channel-switching valve according to the present invention, a channel groove which connects high-pressure liquid flow ports is located on both sides of the rotational center of the rotor. This configuration makes high-pressure liquid flow on both sides of the rotational center of the rotor, so that the locally biased load on the rotor is decreased and the inclination of the rotor is reduced. Therefore, the contact surface will not be scraped off by the edge of the opening of a port during the rotation of the rotor, so that the shortening of the life of the rotor due to a local abrasion will not occur.

BRIEF DESCRIPTION OF THE DRAWINGS

FIG. 3 is a sectional view of the channel-switching valve in a high-pressure liquid-feeding process.

FIG. 8 is a plan view of the contact surface of a rotor in contact with a stator according to the first variation of the first embodiment of the present invention.

FIG. 9 is a plan view of the contact surface of a rotor in contact with a stator according to the second variation of the first embodiment of the present invention.

FIG. 10 is a plan view of the contact surface of a rotor in contact with a stator according to the third variation of the first embodiment of the present invention.

FIG. 13 is a diagram illustrating the channel-switching operation using the channel-switching valve according to the second embodiment of the present invention.

BEST MODE FOR CARRYING OUT THE INVENTION

Figure 1:
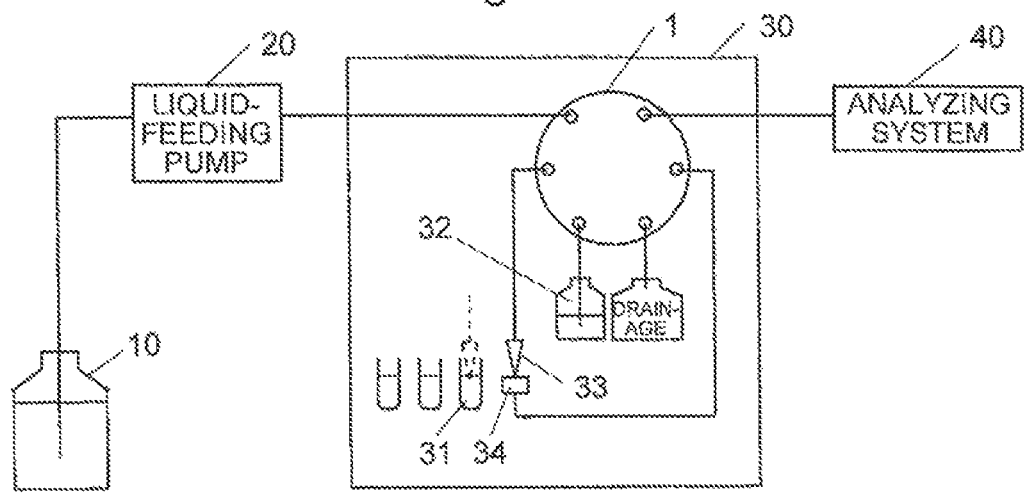
FIG. 1 is a schematic diagram of a channel for liquid samples in the process of analyzing the liquid samples.
Figure 2A:
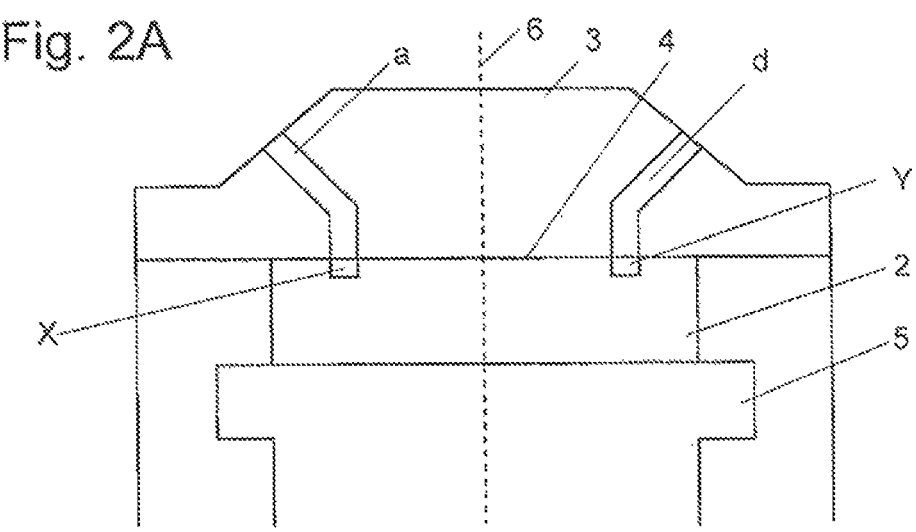
FIG. 2A is a sectional view of a channel-switching valve.
Figure 2B:
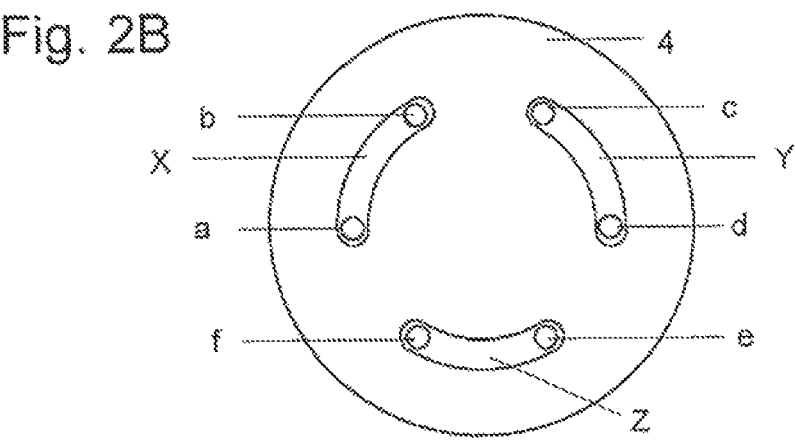
FIG. 2B is a plan view of the contact surface of a rotor in contact with a stator.
Figure 4A:
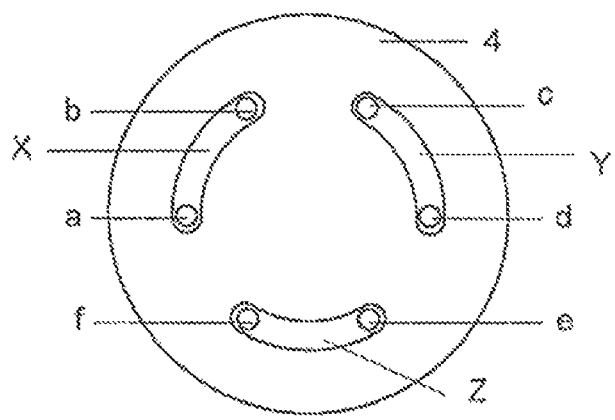
FIGS. 4A-4D are plan views of the contact surface of the rotor in contact with the stator, illustrating the switching operation from the position where ports a and b communicate with each other to the position where ports a and f communicate with each other.
Figure 4B:
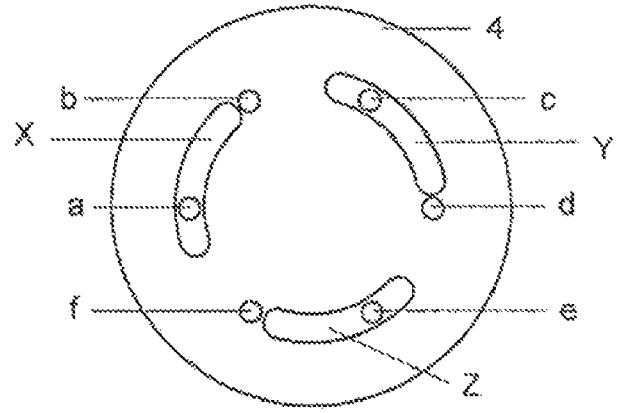
Figure 4C:
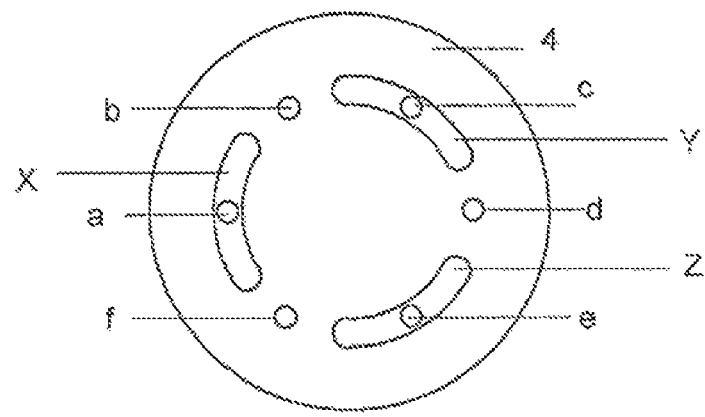
Figure 4D:
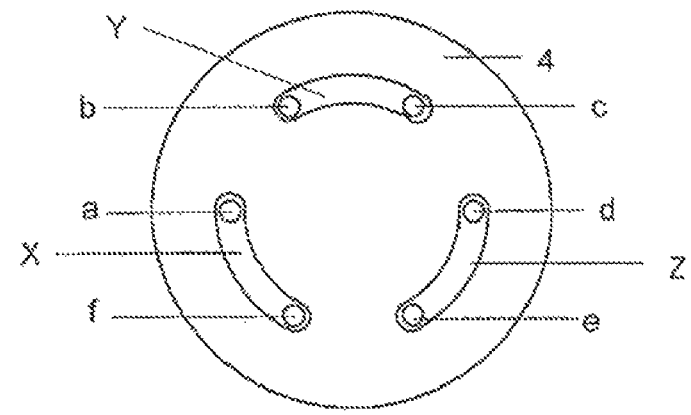
Figure 5A:
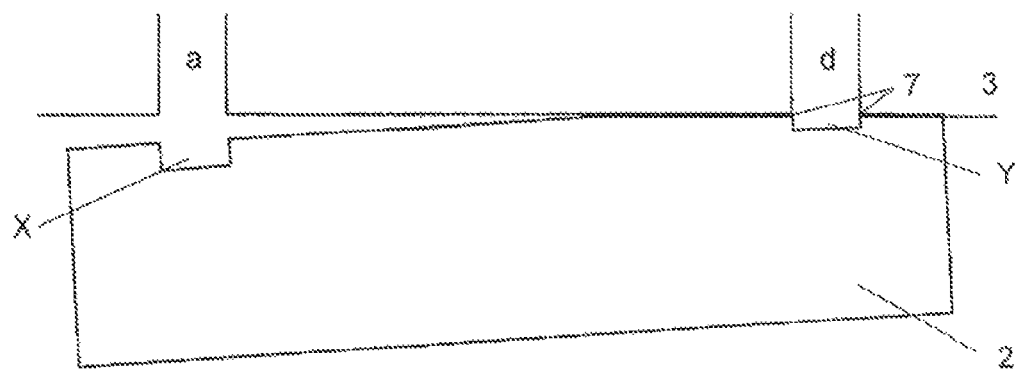
FIG. 5A is a sectional view of a portion near the contact surface of the rotor and the stator at the position where ports a and b communicate with each other.
Figure 5B:
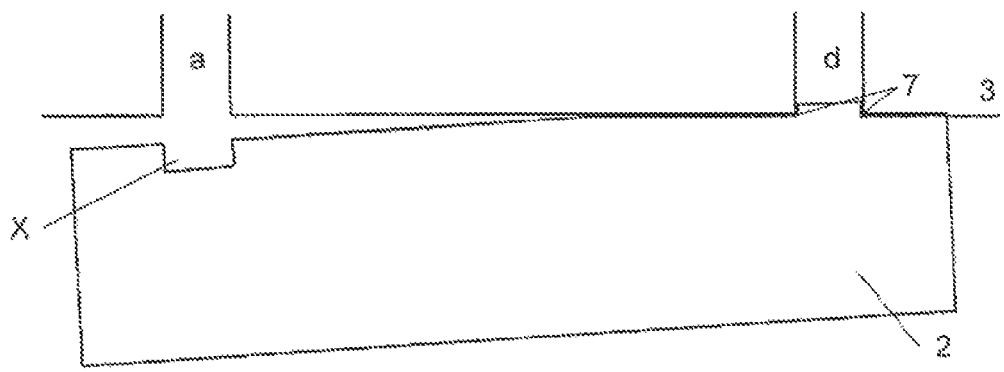
FIG. 5B is a sectional view of the portion near the contact surface of the rotor and the stator at a position in the middle of the switching operation from the position shown in FIG. 5A.
Figure 6A:
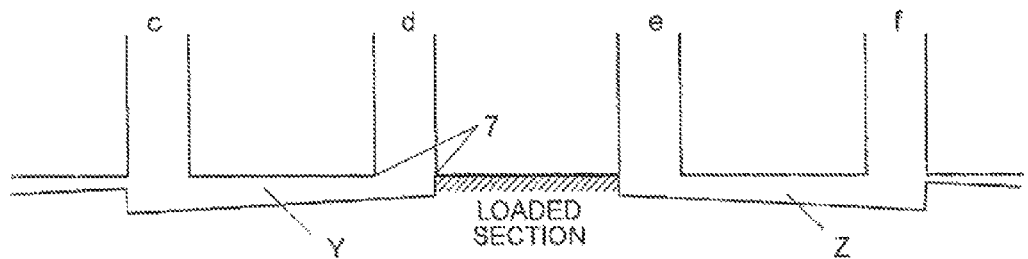
FIGS. 6A-6D are sectional views along the channel grooves near the contact surface of the rotor and the stator, illustrating the switching operation from the position where ports a and b communicate with each other to the position where ports a and f communicate with each other.
Figure 6B:
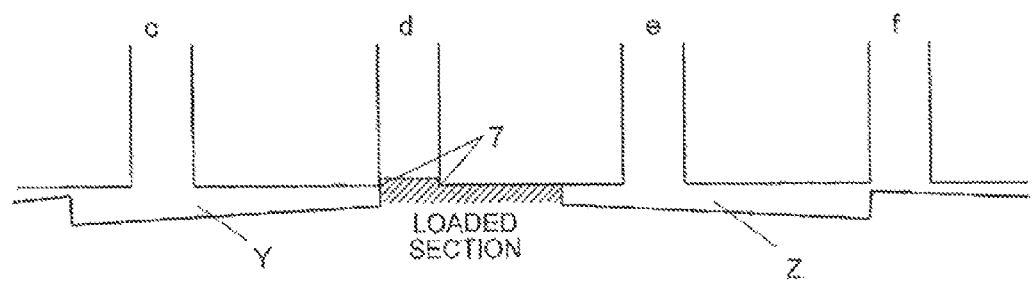
Figure 6C:
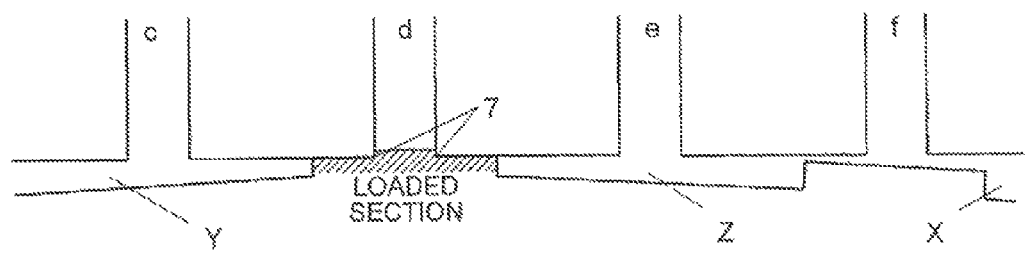
Figure 6D:
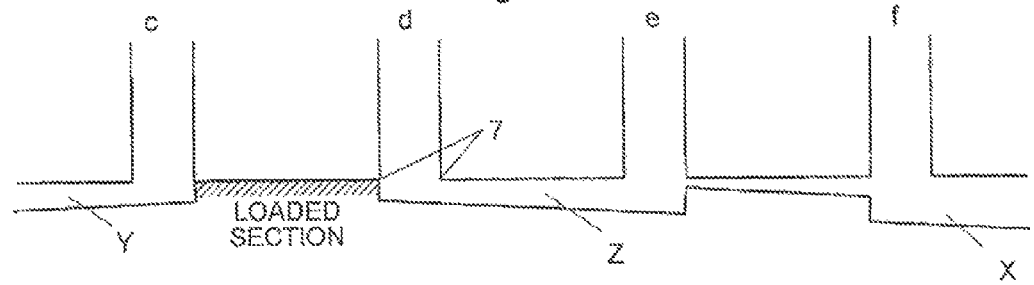

Embodiments of the present invention are hereinafter described. It should be noted that the stators of the switching valves according to the following embodiments have substantially the same configuration as that of the conventional valve and hence will not be shown in the drawings. The same portions of the valve as those of the conventional valve shown in FIGS. 1-4D are denoted by the same numerals.

First Embodiment

Figure 7A:
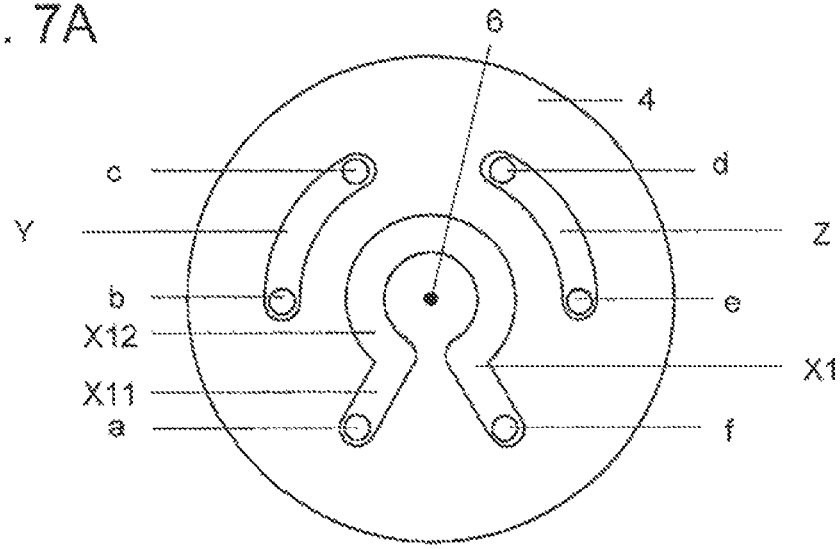
FIG. 7A is a plan view of the contact surface of a rotor in contact with a stator according to the first embodiment of the present invention.
Figure 7B:
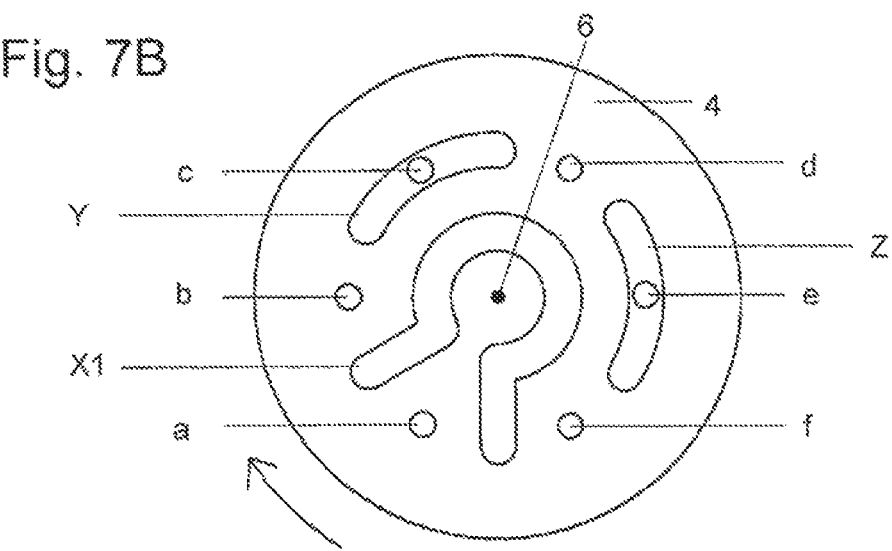
FIG. 7B is a plan view of the contact surface of the rotor in contact with the stator in the middle of the channel-switching operation.
Figure 7C:
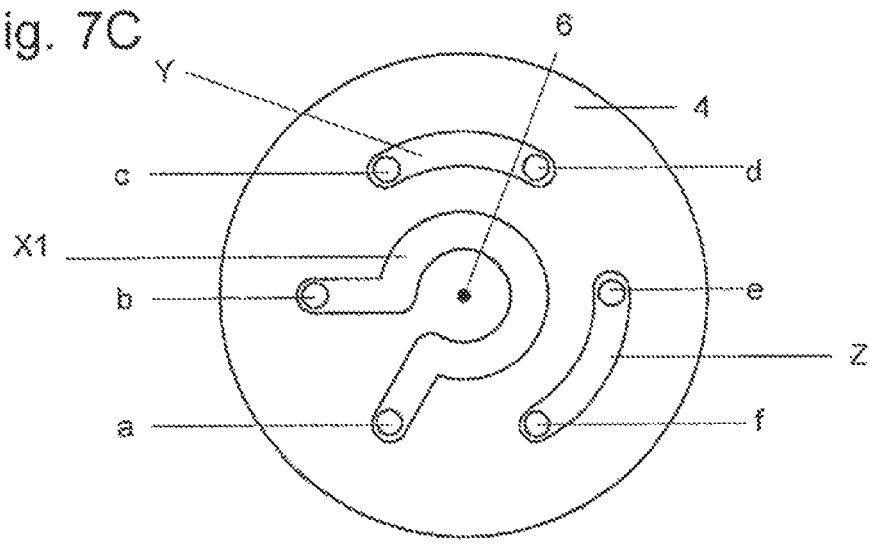
FIG. 7C is a plan view of the contact surface of the rotor in contact with the stator after the channel-switching operation.

FIGS. 7A-7C show the contact surface 4 of the rotor 2 in contact with the stator 3 of a channel-switching valve 1 with six ports according to the first embodiment of the present invention. Three channel grooves X1, Y and Z are formed on the contact surface 4. Also shown are the openings of the ports a-f provided in the stator 3.

A channel extending from a high-pressure liquid-feeding pump 20 is connected to the port a. The channel groove X1, which is designed to be connected to the high-pressure port a, consists of two straight grooves X11 and an arc-shaped groove X12. The grooves X11 respectively extend from the openings of the thereby connected ports a and f toward the rotational center 6, while the groove X12 extends along a major arc connecting the two grooves X11 extended toward the rotational center (FIG. 7A).

To switch the ports, the rotor 2 should be revolved clockwise from the position shown in FIG. 7A by approximately 60 degrees. FIG. 7B shows a position in the middle of the switching operation, and FIG. 7C shows the position after the switching operation is completed. Until immediately before the switching of the channel, high-pressure liquid continues flowing through the high-pressure port a into the channel groove X1, causing a high-pressure load on the channel groove X. However, in the first embodiment, the inclination of the contact surface 4 of the rotor 2 is smaller than in the case of the conventional switching valve, because the channel groove X1 is located on both sides of the rotational center and the portion undergoing the high-pressure load on the contact surface 4 of the rotor 2 is distributed on both sides of the rotational center. Therefore, the contact surface 4 will not be scraped off by the edge of the opening of the port during the rotation of the rotor 2.

Variations of the first embodiment are shown in FIGS. 8-11.

The channel groove X2 of the first variation (FIG. 8) consists of an arc-shaped grove X21 and a circular groove X23 connected by a straight groove X22. The groove X21, which is similar to the groove of the conventional channel-switching valve, is a groove connecting the openings of the ports along the shortest arc-shaped path. The groove X23 is a circular groove whose center is at the rotational center 6. The groove X22 linearly connects the central point of the groove X21 and the groove X23. This first variation also has the effect of reducing the inclination of the rotor 2 during the high-pressure liquid-feeding process, because the channel groove X2 is located on both sides of the rotational center 6.

The channel grooves of the first variation can be more easily machined than those of the first embodiment or the other variations described later.

The channel groove X3 according to the second variation (FIG. 9) is a U-shaped groove connecting the openings of the thereby connected ports by way of an area on the opposite side of the rotational center 6. The shape of the channel groove X3 is similar to that of the channel groove X1 of the first embodiment in that it consists of two straight grooves X31 and an arc-shaped groove X32. However, in the first embodiment, since the straight grooves X11 extend toward the rotational center 6, it is necessary to perform the machining work over a greater length to create the arc-shaped groove X12 extending in the rotational direction. As compared to the first embodiment, the machining work for the channel groove X3 of the second variation is somewhat easier. This second variation also has the effect of reducing the inclination of the rotor 2 during the high-pressure liquid-feeding process.

The channel groove X4 according to the third variation (FIG. 10) also consists of two straight grooves X41 and an arc-shaped groove X42. Each of the straight grooves X41 extends from the opening of a port toward the circumference of the contact surface. The groove X42 extends along a major arc connecting the outer ends of the two grooves X41 and is located farther out than the channel grooves Y and Z.

Since the channel groove X4 of this third variation is formed on the outer side of the other channel grooves Y and Z of the contact surface 4, its machining work will be difficult if there is not a sufficient area on the outer side of the other channel grooves Y and Z. Furthermore, creating the channel groove X4 over a large area on the contact surface 4 may possibly decrease the strength of the contact surface 4. However, among the first embodiment and its variations, the channel groove X4 of this third embodiment is very effective for dispersing the pressure since this groove is formed over the largest area on the contact surface 4. Accordingly, the inclination of the contact surface of the rotor 2 will be the slightest among the first embodiment and its variations.

Figure 11:
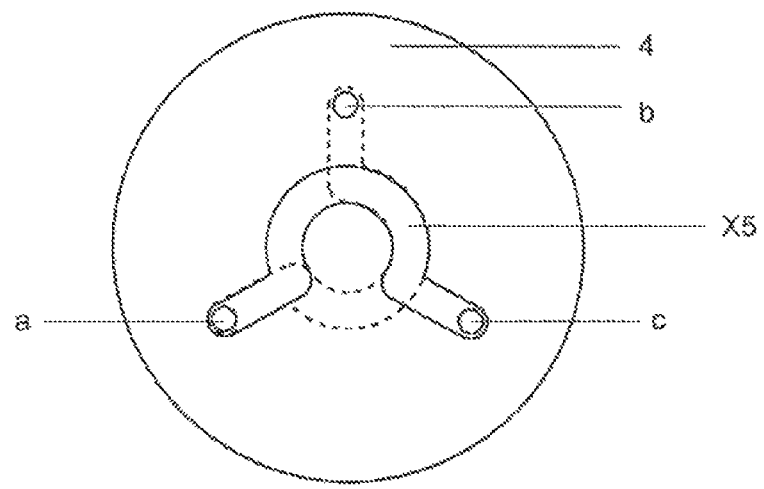
FIG. 11 is a plan view of the contact surface of a rotor in contact with a stator according to the fourth variation of the first embodiment of the present invention.

The fourth variation shown in FIG. 11 is a channel-switching valve having only one channel groove on the contact surface 4. The shape of the channel groove X5 is similar to that of the channel groove X1 of the first embodiment shown in FIGS. 7A-7C. The solid line indicates the position where the high-pressure port a is connected to the port c via the channel groove X5, while the dashed line shows the state after the rotor 2 is rotated to the position where the high-pressure port a is connected to the port b. The channel-switching valve according to this variation also has the effect of reducing the local load on the rotor during the high-pressure water-feeding process.

In any of the previously described variations, the channel groove to which a high-pressure port is connected is located on both sides of the rotational center 6, so that only a gentle inclination of the rotor 2 occurs during the high-pressure liquid-feeding process. Accordingly, the contact surface 4 will not be scraped off by the edge 7 of the opening of the port during the rotation of the rotor 2.

Second Embodiment

Figure 12:
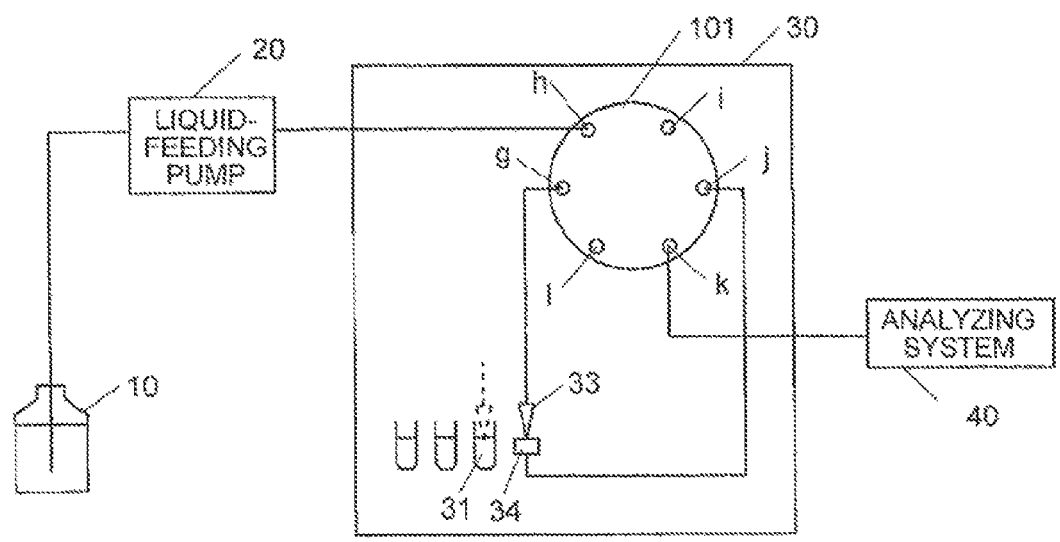
FIG. 12 is a channel configuration diagram of a system using a channel-switching valve according to the second embodiment of the present invention.

FIG. 12 is a channel configuration diagram of a system using a channel-switching valve 101 according to the second embodiment of the present invention. A valve as shown in FIG. 13 is used as the channel-switching valve 101, in which a disk-shaped rotor having channel grooves P, Q1 and Q2 is mounted on a disk-shaped stator having six ports g-l and is rotated while sliding on the stator. In the case of the channel-switching valve 101 according to the second embodiment, the liquid-feeding pump 20 and the analyzing system 40 are respectively connected to the mutually opposing ports h and k, the sampling needle 33 is connected to the port g next to the port h, and the injection port 34 is connected to the port j opposite to the port g. In the present embodiment, the contact surface 104 of the rotor and the stator will look as shown in FIG. 13. The construction of the rotor and the stator is basically the same as shown in FIG. 3 and hence will not be described.

The channel groove P on the rotor connects two mutually opposing ports along a straight line passing through the rotational center 6 of the rotor. Each of the other channel grooves Q1 and Q2 is an arc-shaped groove connecting the neighboring ports. These two grooves are line-symmetrically arranged with respect to the channel groove P.

FIG. 13 is a diagram illustrating a channel-switching operation using the channel-switching valve according to the present embodiment, where (a) shows the channel configuration in loading a sample from a sample container 31, (c) shows the channel configuration in injecting the sample, and (b) and (d) each show the contact surface 104 in the middle of the switching operation. The thick lines indicate the channels under high-pressure load.

In the sample-loading state (a) shown in FIG. 13, the high-pressure port h, to which the liquid-feeding pump 20 is connected, is open to the straight channel groove P, allowing a high-pressure mobile phase to flow through the channel groove P into the analyzing system 40. The ports g and j, to which the sampling needle 33 and the injection port 34 are connected, are respectively open to the arc-shaped channel grooves Q1 and Q2, allowing the sample in the sample container 31 to be sucked from the sampling needle 33 and loaded through the injection port 34 into a sample loop (not shown).

To switch from the sample-loading state (a) to the injection state (c), the rotor should be revolved clockwise from the position of (a) by approximately 60 degrees. Part (b) of FIG. 13 shows the state of the channel-switching valve 101 in the middle of the switching operation. Until immediately before the switching of the channel, a high-pressure load acts on the channel groove P. Since the channel groove P lies on a straight line passing through the rotational center 6, the area undergoing the high-pressure load on the contact surface 104 of the rotor is evenly distributed with respect to the rotational center 6. Accordingly, when the rotor is rotated, the contact surface 4 will not be scraped off by the edge of the opening of the port.

In the injection state (c), an amount of sample loaded into the sample loop in the sample-loading state (a) is carried by the mobile phase coming from the sample feeder 20, to be injected into the analyzing system 40. The high-pressure port h, to which the liquid-feeding pump 20 is connected, is open to the arc-shaped channel groove Q1, allowing the high-pressure mobile phase to flow from the channel groove Q1 through the injection port 34 into the channel groove Q2. Accordingly, a high-pressure load acts on the channel groves Q1 and Q2 in the injection state (c). However, even in the state (d), i.e. in the middle of the switching-operation from the injection state (c) to the sample-loading state (a), the contact surface 104 will not be scraped off during the rotation of the rotor since the channel grooves Q1 and Q2 undergoing the high-pressure load are evenly distributed on both sides of the rotational axis.

It should be noted that the preset invention is not limited to the previously described embodiments and variations. Their configurations can be appropriately changed within the spirit of the present invention. For example, although the channel-switching valves of the previous embodiments are six-port valves, it is naturally possible to increase the number of the ports.

EXPLANATION OF NUMERALS 1, 101 . . . Channel-Switching Valve
2 . . . Rotor
3 . . . Stator
4, 104 . . . Contact Surface of Rotor and Stator
5 . . . Shaft
6 . . . Rotational Center of Rotor
7 . . . Edge of High-Pressure Port
10 . . . Mobile Phase Container
20 . . . Liquid-feeding pump
30 . . . Sample Injector
31 . . . Sample Container
32 . . . Washing Liquid Container
33 . . . Sampling Needle
34 . . . Injection Port
40 . . . Analyzing System
a-f, g-l . . . Port
X-Z, P, Q1, Q2 . . . Channel Groove

The invention claimed is:

1. A liquid chromatograph system including:
a liquid chromatograph;
a liquid-feeding pump for sucking a mobile-phase solution and ejecting the mobile-phase solution into a channel so as to supply the mobile-phase solution through the channel into the liquid chromatograph; and
a channel-switching valve for switching a state of the channel between an injection state in which the channel is configured so that the mobile-phase solution with a sample flows into the liquid chromatograph and a sample-loading state in which the channel is configured so that the mobile-phase solution without any sample flows into the liquid chromatograph,
wherein:
the channel-switching valve includes a stator and a rotor which has a surface in contact with one surface of the stator and rotates while sliding on the contact surface;
the stator has a plurality of liquid flow ports open to the contact surface;
the rotor has a plurality of channel grooves fir connecting the liquid flow ports; and
the channel groove into Which the mobile-phase solution flows in the sample-loading state surrounds a rotational center of the rotor so that the channel groove is located on both sides of the rotational center of the rotor.

2. A liquid chromatograph system including:
a liquid chromatograph;
a liquid-feeding pump for sucking a mobile-phase solution and ejecting the mobile-phase solution into a channel so as to supply the mobile-phase solution through the channel into the liquid chromatograph; and
a channel-switching valve for switching a state of the channel between a high-pressure state in which the channel is configured so that a high-pressure liquid flows into the liquid chromatograph and a low-pressure state in which the channel is configured so that a low-pressure liquid flows into the liquid chromatograph,
wherein:
the channel-switching valve includes a stator and a rotor which has a surface in contact with one surface of the stator and rotates while sliding on the contact surface;
the stator has a plurality of liquid flow ports open to the contact surface;

the rotor has a plurality of channel grooves for connecting the liquid flow ports; and the channel groove into which the liquid flows in the high-pressure state surrounds a rotational center of the rotor so that the channel groove is located on both sides of the rotational center of the rotor.

* * * * *

UNITED STATES PATENT AND TRADEMARK OFFICE
CERTIFICATE OF CORRECTION

PATENT NO. : 8,382,979 B2
APPLICATION NO. : 13/541193
DATED : February 26, 2013
INVENTOR(S) : Yoshiaki Maeda, Kenichi Yasunaga and Shinji Tanaka It is certified that error appears in the above-identified patent and that said Letters Patent is hereby corrected as shown below:

Title Page, item (75), one of the named inventors, Yoshiki Maeda, should read: Yoshiaki Maeda.

Signed and Sealed this
First Day of October, 2013

Teresa Stanek Rea
*Deputy Director of the United States Patent and Trademark Office*